(12) United States Patent
Akagane

(10) Patent No.: US 9,358,407 B2
(45) Date of Patent: Jun. 7, 2016

(54) ULTRASONIC ACTUATED UNIT AND ULTRASONIC TREATMENT DEVICE

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/524,266

(22) Filed: Oct. 27, 2014

(65) Prior Publication Data

US 2015/0045701 A1    Feb. 12, 2015

Related U.S. Application Data

(63) Continuation of application No. PCT/JP2013/067896, filed on Jun. 28, 2013.

(60) Provisional application No. 61/704,894, filed on Sep. 24, 2012.

(51) Int. Cl.
*A61B 17/32* (2006.01)
*B06B 1/06* (2006.01)
*A61N 7/00* (2006.01)
*A61B 19/00* (2006.01)

(52) U.S. Cl.
CPC .......... *A61N 7/00* (2013.01); *A61B 17/320068* (2013.01); *B06B 1/0644* (2013.01); *A61B 2017/320072* (2013.01); *A61B 2017/320088* (2013.01); *A61B 2019/4889* (2013.01)

(58) Field of Classification Search
CPC ............. A61N 7/00; A61N 2007/0073; A61B 17/320068; A61B 17/22004; A61B 17/22012; A61B 2017/320084; A61B 2017/320088; A61B 2017/320072; A61B 2017/32008; A61B 2017/320096; A61B 2017/22014; A61B 2017/22015; A61B 2017/22024; A61B 2017/22027; A61B 2017/00106; A61B 2017/0011; A61B 8/44; A61F 9/00745; B06B 1/064; B06B 2201/76
USPC ............................................... 606/169; 601/2
See application file for complete search history.

(56) References Cited

U.S. PATENT DOCUMENTS 5,123,903 A  *  6/1992  Quaid ............ A61B 17/320068
                                                           604/22
6,328,703 B1 * 12/2001  Murakami ..... A61B 17/320068
                                                            601/2

(Continued)

FOREIGN PATENT DOCUMENTS

CN          101596521 A    12/2009
JP       A-2001-161705      6/2001

(Continued)

OTHER PUBLICATIONS

Apr. 2, 2015 International Preliminary Report on Patentability issued in International Application No. PCT/JP2013/067896.

(Continued)

*Primary Examiner* — Melanie Tyson
*Assistant Examiner* — Katherine Schwiker
(74) *Attorney, Agent, or Firm* — Oliff PLC

(57) ABSTRACT

An ultrasonic actuated unit includes an intermediary portion continuous with an ultrasonic transmitting portion or connected to the ultrasonic transmitting portion at a node position of a longitudinal vibration, and a noncontact vibrating portion extending in directions parallel to a longitudinal axis without contacting the ultrasonic transmitting portion, an imprecise vibration being transmitted to the noncontact vibrating portion from the ultrasonic transmitting portion via the intermediary portion. The ultrasonic actuated unit includes a vibration absorbing portion absorbing the imprecise vibration transmitted to the noncontact vibrating portion.

13 Claims, 8 Drawing Sheets

(56) References Cited

U.S. PATENT DOCUMENTS

| | | | |
|---|---|---|---|
| 6,508,775 B2 | 1/2003 | McKenzie et al. | |
| 2005/0033201 A1 | 2/2005 | Takahashi et al. | |
| 2009/0299395 A1* | 12/2009 | Hirai et al. | 606/169 |
| 2011/0288451 A1* | 11/2011 | Sanai et al. | 601/2 |
| 2014/0167561 A1 | 6/2014 | Hirai et al. | |

FOREIGN PATENT DOCUMENTS

| | | |
|---|---|---|
| JP | A-2002-065688 | 3/2002 |
| JP | A-2005-066316 | 3/2005 |
| JP | A-2005-137481 | 6/2005 |
| JP | B2-4249064 | 4/2009 |

OTHER PUBLICATIONS

Jul. 23, 2013 International Search Report issued in International application No. PCT/JP2013/067896.

Feb. 14, 2016 Office Action issued in Chinese Patent Application No. 201380028594.0.

* cited by examiner

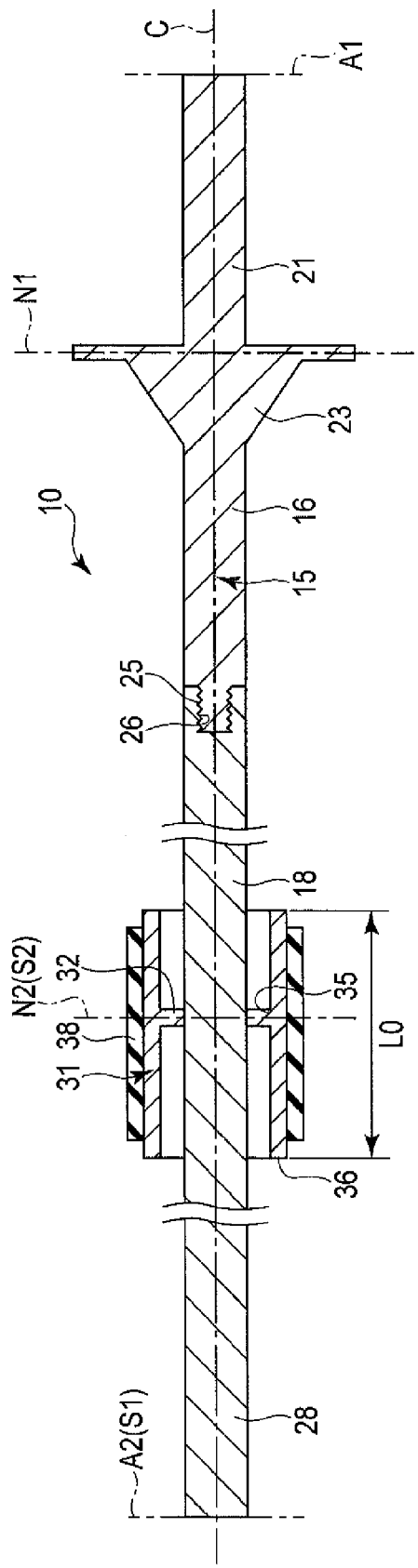
F I G. 4

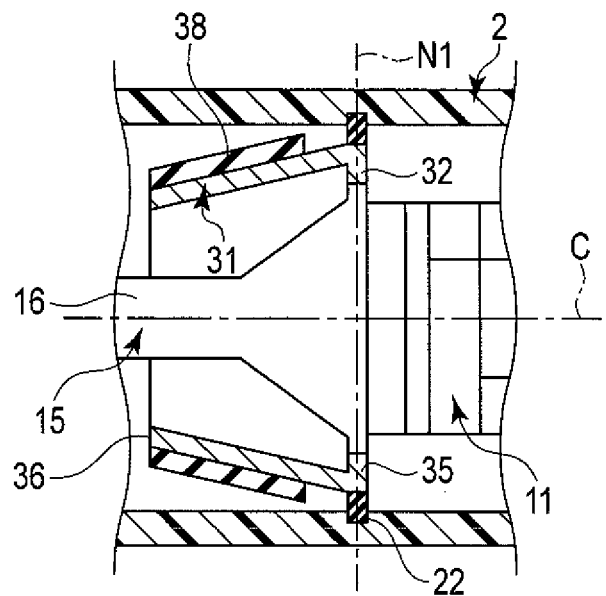
F I G. 7
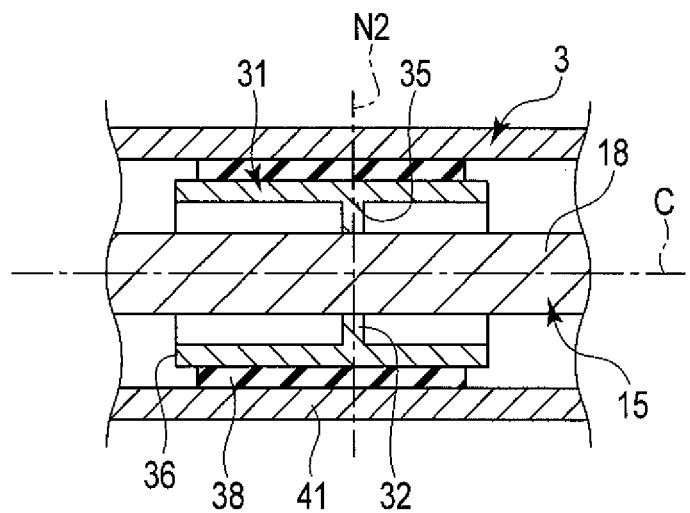
F I G. 8

ULTRASONIC ACTUATED UNIT AND ULTRASONIC TREATMENT DEVICE

CROSS-REFERENCE TO RELATED APPLICATIONS

This is a Continuation Application of PCT Application No. PCT/JP2013/067896, filed Jun. 28, 2013 and based upon and claiming the benefit of priority from prior U.S. Provisional Applications No. 61/704,894, filed Sep. 24, 2012, the entire contents of which are incorporated herein by reference.

BACKGROUND OF THE INVENTION

1. Field of the Invention

The present invention relates to an ultrasonic actuated unit including an ultrasonic transmitting portion which extends along a longitudinal axis and which can transmit an ultrasonic vibration from a proximal direction toward a distal direction, wherein the ultrasonic actuated unit is actuated when the ultrasonic vibration is transmitted. The present invention also relates to an ultrasonic treatment device including the ultrasonic actuated unit.

2. Description of the Related Art

Japanese Patent No. 4249064 has disclosed an ultrasonic actuated unit which is actuated when the ultrasonic vibration is transmitted. This ultrasonic actuated unit includes an ultrasonic transmitting portion which can transmit an ultrasonic vibration from a proximal direction toward a distal direction. The ultrasonic transmitting portion includes a horn member serving as a proximal-side transmitting member to which an ultrasonic vibrator that is an ultrasonic generating portion is attached, and a probe serving as a distal-side transmitting member which is connected to the distal direction side of the horn member. The ultrasonic transmitting portion is inserted through a channel of an endoscope. A distal treatment section is provided in a distal portion of the probe, and when the ultrasonic vibration is transmitted to the distal treatment section, a treatment target such as a living tissue is treated by the use of the ultrasonic vibration. When the ultrasonic vibration is transmitted, the ultrasonic transmitting portion performs a longitudinal vibration having a vibration direction parallel to the longitudinal axis at a predetermined reference frequency.

A vibration absorbing member is disposed on an outer peripheral portion of the probe of the ultrasonic transmitting portion at a node position of the longitudinal vibration. The vibration absorbing member is in abutment with an inner peripheral portion of the channel. Here, in the ultrasonic actuated unit, the shape of the ultrasonic transmitting portion about the longitudinal axis may be partly asymmetric, or the material quality of the ultrasonic transmitting portion may be partly nonuniform. In this case, in addition to the longitudinal vibration, an imprecise vibration having a vibration direction which is not parallel to the longitudinal axis is generated. When the imprecise vibration is generated, the imprecise vibration is absorbed by the vibration absorbing member. Since the vibration absorbing member is located at the node position of the longitudinal vibration, the longitudinal vibration is not absorbed by the vibration absorbing member.

BRIEF SUMMARY OF THE INVENTION

According to one aspect of the invention, an ultrasonic actuated unit includes that: an ultrasonic transmitting portion which extends along a longitudinal axis and which is configured to perform a longitudinal vibration having a vibration direction parallel to the longitudinal axis at a predetermined reference frequency when an ultrasonic vibration is transmitted from a proximal direction toward a distal direction; an intermediary portion which is continuous with the ultrasonic transmitting portion or connected to the ultrasonic transmitting portion at a node position of the longitudinal vibration; a noncontact vibrating portion which extends in directions parallel to the longitudinal axis without contacting the ultrasonic transmitting portion, an imprecise vibration being configured to be transmitted to the noncontact vibrating portion from the ultrasonic transmitting portion via the intermediary portion, the imprecise vibration having a vibration direction which is not parallel to the longitudinal axis, the noncontact vibrating portion having an axially parallel dimension different in value from a natural number multiple of a half wavelength of the longitudinal vibration at the reference frequency in the directions parallel to the longitudinal axis so that the noncontact vibration portion does not perform the longitudinal vibration at the reference frequency when the ultrasonic vibration is transmitted via the intermediary portion; and a vibration absorbing portion which is attached to the noncontact vibrating portion and which is configured to absorb the imprecise vibration transmitted to the noncontact vibrating portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a sectional view schematically showing a configuration of an ultrasonic actuated unit according to the first embodiment;

FIG. 7 is a sectional view schematically showing an internal configuration of a vibrator case according to a second modification of the first embodiment;

FIG. 8 is a sectional view schematically showing an internal configuration of a sheath according to a second embodiment;

DETAILED DESCRIPTION OF THE INVENTION (First Embodiment)

Figure 1:
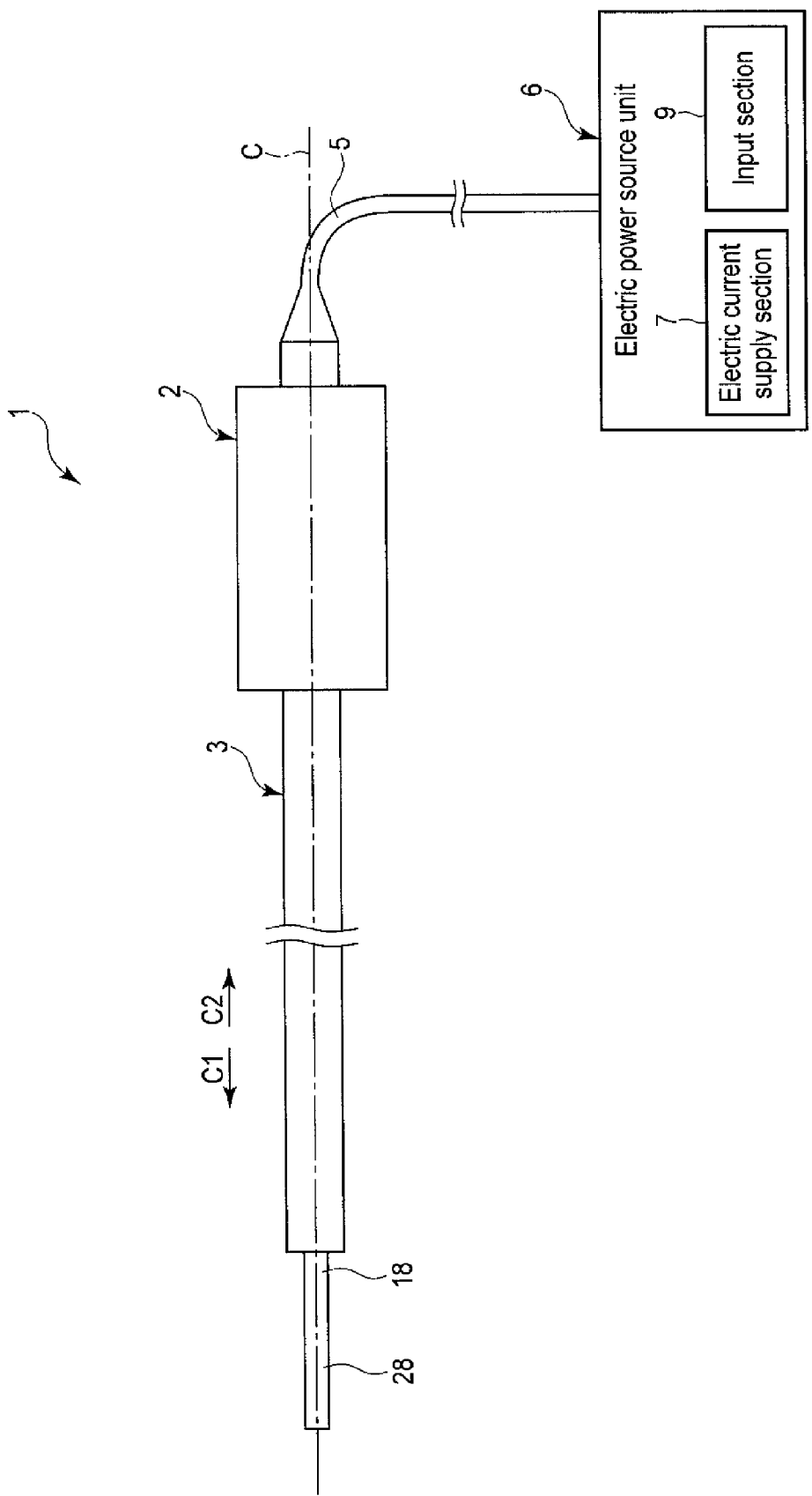
FIG. 1 is a schematic diagram showing an ultrasonic treatment device according to a first embodiment of the present invention.

A first embodiment of the present invention is described with reference to FIG. 1 to FIG. 5. FIG. 1 is a diagram showing an ultrasonic treatment device 1 according to the present embodiment. As shown in FIG. 1, the ultrasonic treatment device 1 has a longitudinal axis C. Here, one of two directions parallel to the longitudinal axis C is a distal direction (direction of an arrow C1 in FIG. 1), and a direction opposite to the distal direction is a proximal direction (direction of an arrow C2 in FIG. 1). The ultrasonic treatment device 1 includes a vibrator case 2, and a sheath 3 attached to the distal direction side of the vibrator case 2. The sheath 3 extends along the longitudinal axis C. One end of a cable 5 is connected to a proximal end of the vibrator case 2. The other end of the cable 5 is connected to an electric power source unit 6. The electric power source unit 6 includes an electric current supply section 7 and an input section 9.

Figure 2:
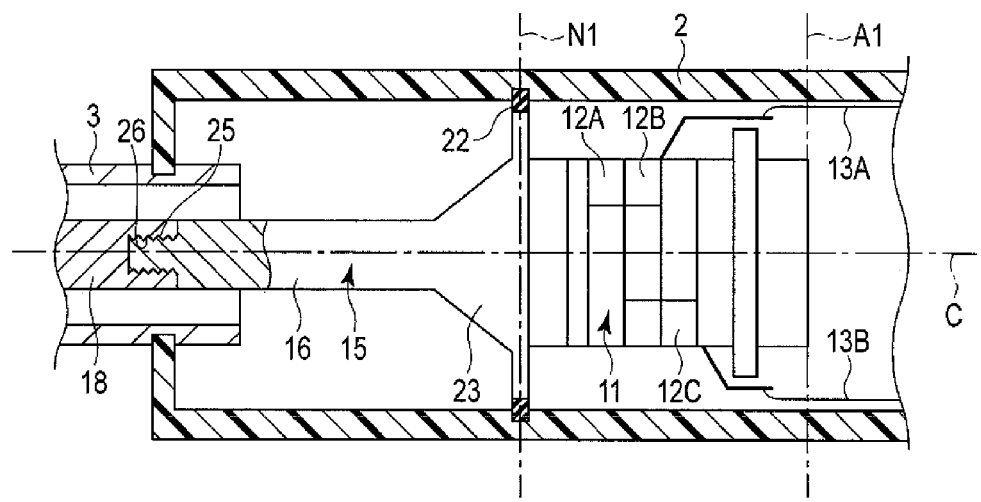
FIG. 2 is a sectional view schematically showing an internal configuration of a vibrator case according to the first embodiment.

FIG. 2 is a diagram showing an internal configuration of the vibrator case 2. As shown in FIG. 1 and FIG. 2, an ultrasonic actuated unit 10 extends inside the oscillator case 2 and inside the sheath 3. Inside the vibrator case 2, an ultrasonic vibrator 11, which is an ultrasonic generating portion, is attached to the ultrasonic actuated unit 10. The ultrasonic vibrator 11 includes piezoelectric elements 12A to 12C which are configured to convert a current to an ultrasonic vibration. One end of each electric wiring lines 13A and 13B is connected to the ultrasonic oscillator 11. The other end of each of the electric wiring lines 13A and 13B is connected to the electric current supply section 7 of the electric power source unit 6 through an inside of the cable 5. The ultrasonic vibration is generated in the ultrasonic vibrator 11 by the supply of an electric current to the ultrasonic vibrator 11 from the electric current supply section 7 via the electric wiring lines 13A and 13B.

Figure 3:
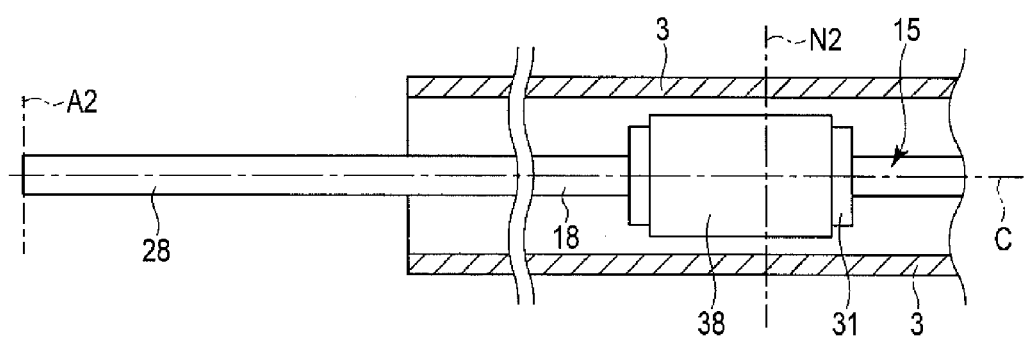
FIG. 3 is a sectional view schematically showing an internal configuration of a sheath according to the first embodiment.

FIG. 3 is a diagram showing an internal configuration of the sheath 3. FIG. 4 is a diagram showing a configuration of the ultrasonic actuated unit 10. As shown in FIG. 2 to FIG. 4, the ultrasonic operated unit 10 includes an ultrasonic transmitting portion 15 extending along the longitudinal axis C. The ultrasonic transmitting portion 15 includes a horn member 16 serving as a proximal-side transmitting member to which the ultrasonic vibrator 11 is attached, and a probe 18 serving as a distal-side transmitting member which is connected to the distal direction side of the horn member 16. The ultrasonic vibration generated in the ultrasonic oscillator 11 is transmitted to the horn member 16 of the ultrasonic transmitting portion 15. In the ultrasonic transmitting portion 15, the ultrasonic vibration is transmitted from the proximal direction toward the distal direction.

When the ultrasonic vibration is transmitted to the horn member 16, the ultrasonic actuated unit 10 is actuated. When the ultrasonic vibration is transmitted, the ultrasonic transmitting portion 15 performs a longitudinal vibration having a vibration direction parallel to the longitudinal axis C at a predetermined reference frequency $f0$. Therefore, in the ultrasonic transmitting portion 15, a proximal end of the horn member 16 (a proximal end of the ultrasonic transmitting portion 15) serves as an anti-node position A1 of the longitudinal vibration at the reference frequency $f0$, and a distal end of the probe 18 (a distal end of the ultrasonic transmitting portion 15) serves as an anti-node position A2 of the longitudinal vibration at the reference frequency $f0$.

As shown in FIG. 2 and FIG. 4, a vibrator attachment portion 21 is provided in the horn member 16. When the oscillator attachment portion 21 is inserted through members constituting the ultrasonic vibrator 11 such as the piezoelectric elements 12A to 12C, the ultrasonic vibrator 11 is attached to the vibrator attachment portion 21 of the horn member 16. The horn member 16 is attached to the vibrator case 2 via an elastic member 22. The horn member 16 is attached to the vibrator case 2 at a node position N1 of the longitudinal vibration at the reference frequency $f0$.

A sectional area varying portion 23 which varies in the sectional area perpendicular to the longitudinal axis C is provided in the horn member 16. The sectional area varying portion 23 is located to the distal direction side with respect to the vibrator attachment portion 21. In the sectional area varying portion 23, the sectional area perpendicular to the longitudinal axis C decreases toward the distal direction. Therefore, the amplitude of the longitudinal vibration is increased by the sectional area varying portion 23. An external thread 25 is formed at a distal portion of the horn member 16.

As shown in FIG. 2, an internal thread 26 is formed at a proximal portion of the probe 18. When the internal thread 26 is screwed into the external thread 25 of the horn member 16, the probe 18 is connected to the distal direction side of the horn member 16. When the probe 18 is connected to the horn member 16, the ultrasonic vibration is transmitted to the probe 18 from the horn member 16.

As shown in FIG. 1 and FIG. 3, the probe 18 extends up to a part located to the distal direction side with respect to a distal end of the sheath 3. That is, the probe 18 which is the distal-side transmitting member is inserted through the sheath 3. A distal treatment section 28 is provided in a distal portion of the probe 18. The ultrasonic vibration transmitted to the probe 18 from the horn member 16 is transmitted toward the distal direction in the probe 18. When the ultrasonic vibration is transmitted to the distal treatment section 28, a treatment target such as a living tissue is treated by the use of the ultrasonic vibration.

As shown in FIG. 3 and FIG. 4, a cylindrical noncontact vibrating portion 31 is provided inside the sheath 3. The noncontact vibrating portion 31 extends along the longitudinal axis C without contacting the probe 18 and the sheath 3. The probe 18 is inserted through the noncontact vibrating portion 31. An intermediary portion 32 is provided between the probe 18 and the noncontact vibration portion 31 in diametrical directions. The intermediary portion 32 is integrated with the noncontact vibrating portion 31, and is connected to the probe 18. Although the intermediary portion 32 and the noncontact vibrating portion 31 are formed separately from the probe 18 in the present embodiment, this is not a limitation. For example, the intermediary portion 32 may be integrated with the probe 18, and the intermediary portion 32 may be continuous with the probe 18 of the ultrasonic transmitting portion 15.

The noncontact vibrating portion 31 includes a vibration receiving portion 35 continuous with the intermediary portion 32. In the noncontact vibration portion 31, a farthest portion 36 is provided at a position farthest from the vibration receiving portion 35. Although the noncontact vibrating portion 31 is integrated with the intermediary portion 32 in the present embodiment, this is not a limitation. For example, the noncontact vibrating portion 31 may be formed separately from the intermediary portion 32, and the vibration receiving portion 35 of the noncontact vibrating portion 31 may be connected to the intermediary portion 32.

The noncontact vibrating portion 31 and the intermediary portion 32 may be made of, for example, titanium, duralumin, or PEEK. That is, the noncontact vibrating portion 31 and the intermediary portion 32 are made of a material which is equal in vibration transmission capability to PEEK or which is higher in vibration transmission capability than PEEK. Therefore, for example, rubber lower in vibration transmission capability than PEEK is not used as the material to form the noncontact vibrating portion 31 and the intermediary portion 32.

Figure 5:
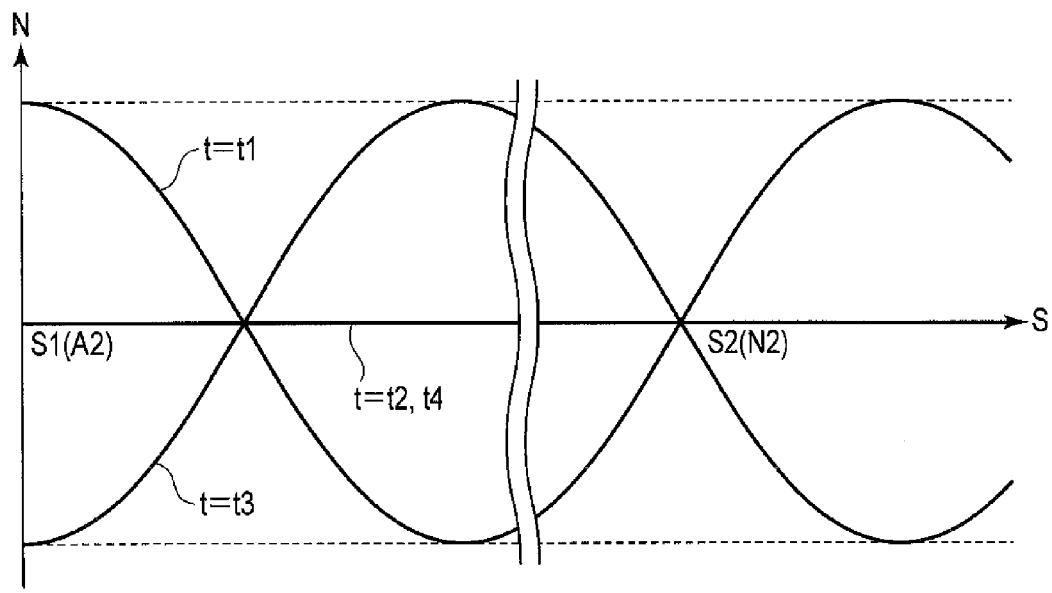
FIG. 5 is a schematic diagram showing changes of a longitudinal vibration relative to changes of the position in a probe along a longitudinal axis according to the first embodiment.

FIG. 5 is a schematic diagram showing changes of the longitudinal vibration (v) relative to changes of a position S in the probe 18 along the longitudinal axis C. In FIG. 5, the longitudinal vibration (v) at times t=t1, t2, t3, and t4 are shown. As shown in FIG. 4 and FIG. 5, the position S1 which is the distal end of the probe 18 (the distal end of the ultrasonic transmitting portion 15) serves as the loop position A2 in the ultrasonic vibration at the predetermined reference frequency f0. A position S2 at which the intermediary portion 32 is connected serves as a node position N2 of the longitudinal vibration. That is, the intermediary portion 32 is connected to the probe 18 of the ultrasonic transmitting portion 15 at the node position N2 of the longitudinal vibration at the reference frequency f0. Since the intermediary portion 32 is connected to the probe 18 at the node position N2 of the longitudinal vibration, the longitudinal vibration is not transmitted to the intermediary portion 32 from the probe 18. When the intermediary portion 32 is integrated with the probe 18, the intermediary portion 32 is also continuous with the probe 18 of the ultrasonic transmitting portion 15 at the node position (N2) of the longitudinal vibration at the reference frequency f0.

As shown in FIG. 3 and FIG. 4, a cylindrical vibration absorbing portion 38 is attached to an outer peripheral direction side of the noncontact vibration portion 31. In the present embodiment, the vibration absorbing portion 38 is located between the noncontact vibrating portion 31 and the sheath 3 in the diametrical directions, and is not in contact with the sheath 3. The vibration absorbing portion 38 extends along the longitudinal axis C, and is in close contact with the outer peripheral portion of the noncontact vibrating portion 31. Most part of the outer peripheral portion of the noncontact vibration portion 31 is covered with the vibration absorbing portion 38. In other words, the vibration absorbing portion 38 is in close contact with the most part of the outer circumferential portion of the noncontact vibrating portion 31. The vibration absorbing portion 38 is made of a material such as rubber lower in vibration transmission capability than PEEK. That is, the vibration absorbing portion 38 is lower in vibration transmission capability than the noncontact vibrating portion 31. Thus, when the noncontact vibrating portion 31 vibrates, the vibration of the noncontact vibrating portion 31 is absorbed by the vibration absorbing portion 38.

In the present embodiment, the vibration absorbing portion 38 is cylindrical, and covers the most part of the outer peripheral portion of the noncontact vibrating portion 31. However, this is not a limitation. For example, a plurality of rod-like vibration absorbing portions 38 extending parallel to the longitudinal axis C may be provided and arranged on the noncontact vibrating portion 31 in a state that the vibration absorbing portions 38 are equally spaced. Alternatively, for example, more than one ring-shaped vibration absorbing portions 38 may be provided and the vibration absorbing portions 38 may be intermittently arranged on the noncontact vibrating portion 31. That is, the vibration absorbing portion 38 has only to be in close contact with at least part of the noncontact vibrating portion 31.

It is preferable that an axially parallel dimension L0 of the noncontact vibrating portion 31 in directions parallel to the longitudinal axis C is different in value from a natural number multiple of a half wavelength of the longitudinal vibration at the reference frequency f0. That is, it is preferable that the dimension L0 of the noncontact vibrating portion 31 is a dimension at which the longitudinal vibration is not performed at the reference frequency f0. Thus, even if the ultrasonic vibration performing the longitudinal vibration at the reference frequency f0 is transmitted to the noncontact vibrating portion 31 from the probe 18 via the intermediary portion 32 because of some problem, the noncontact vibrating portion 31 does not perform the longitudinal vibration at the reference frequency f0. In the present embodiment, the axially parallel dimension L0 of the noncontact vibrating portion 31 is adjusted so that the noncontact vibrating portion 31 does not perform the longitudinal vibration at the reference frequency f0. However, this is not a limitation. For example, the material quality of the noncontact vibrating portion 31 may be adjusted so that the noncontact vibrating portion 31 does not perform the longitudinal vibration at the reference frequency f0.

Now, the functions and advantageous effects of the ultrasonic actuated unit 10 and the ultrasonic treatment device 1 according to the present embodiment are described. When a treatment target such as a living tissue is treated by the ultrasonic treatment device 1 including the ultrasonic actuated unit 10, an electric current is supplied to the ultrasonic vibrator 11 from the electric current supply section 7 via the electric wiring lines 13A and 13B by the operation in the input section 9. As a result, an ultrasonic vibration is generated in the ultrasonic vibrator 11, and the ultrasonic vibration is transmitted to the ultrasonic transmitting portion 15. When the ultrasonic vibration is transmitted to the ultrasonic transmitting portion 15, the ultrasonic actuated unit 10 is actuated. When the ultrasonic vibration is transmitted from the proximal direction toward the distal direction in the ultrasonic transmitting portion 15, the ultrasonic transmitting portion 15 performs a longitudinal vibration at the predetermined reference frequency f0. When the ultrasonic vibration is transmitted to the distal treatment section 28 provided in the distal portion of the probe 18, the distal treatment section 28 treats the treatment target by using the ultrasonic vibration.

Here, in the ultrasonic actuated unit 10, the shape of the ultrasonic transmitting portion 15 about the longitudinal axis C may be partly asymmetric, a material quality such as Young's modulus may be partly nonuniform in the ultrasonic transmitting portion 15, or the working accuracy, for example, the surface roughness of the outer peripheral portion may be nonuniform in the ultrasonic transmitting portion 15. In this case, an inaccuracy vibration having a vibration direction which is not parallel to the longitudinal axis C is generated in addition to the longitudinal vibration. The imprecise vibration includes, for example, a lateral vibration having a vibration direction perpendicular to the longitudinal axis C, a torsional vibration having a vibration direction coinciding with the circumferential directions of the ultrasonic transmitting portion 15, and a surface acoustic wave vibration in which the surface of the ultrasonic transmitting portion 15 only vibrates.

In the present embodiment, when the imprecise vibration is generated in the ultrasonic transmitting portion 15, the inaccuracy vibration is transmitted to the noncontact vibrating portion 31 via the intermediary portion 32. The noncontact vibrating portion 31 receives the imprecise vibration from the intermediary portion 32 by the vibration receiving portion 35 continuous with the intermediary portion 32. The noncontact vibrating portion 31 is made of a material having a high vibration transmission capability. Thus, in the noncontact vibrating portion 31, the imprecise vibration is transmitted to the farthest portion 36 which is located farthest from the vibration receiving portion 35.

The imprecise vibration is then absorbed by the vibration absorbing portion 38 in the noncontact vibrating portion 31. A most part of the outer peripheral portion of the noncontact vibrating portion 31 is covered with the vibration absorbing portion 38. Thus, the imprecise vibration is efficiently absorbed by the vibration absorbing portion 38, and the inaccuracy vibration is effectively damped in the noncontact vibrating portion 31. Here, when the noncontact vibrating portion 31 performs the imprecise vibration, the ultrasonic transmitting portion 15 and the intermediary portion 32 perform the imprecise vibration in resonance with the noncontact vibrating portion 31. Therefore, if the imprecise vibration is damped in the noncontact vibrating portion 31, the imprecise vibration is effectively damped in the ultrasonic transmitting portion 15 and the intermediary portion. If the inaccuracy vibration is effectively damped in the ultrasonic transmitting portion 15, a treatment performance in the distal treatment section 28 can be ensured, and the strength of the ultrasonic transmitting portion 15, for example, of the probe 18 can be ensured.

The intermediary portion 32 is connected to the probe 18 of the ultrasonic transmitting portion 15 at the node position N2 of the longitudinal vibration at the reference frequency f0. Thus, the longitudinal vibration is not transmitted to the intermediary portion 32 from the probe 18, and the longitudinal vibration at the reference frequency f0 in the ultrasonic transmitting portion 15 is not transmitted to the noncontact vibrating portion 31. Since the longitudinal vibration is not transmitted to the noncontact vibrating portion 31, the longitudinal vibration is not absorbed by the vibration absorbing portion 38. Therefore, the longitudinal vibration is not damped in the ultrasonic transmitting portion 15, and the ultrasonic transmitting portion 15 properly performs the longitudinal vibration. As a result, a treatment performance in the distal treatment section 28 can be ensured.

When the ultrasonic transmitting portion 15 performs the longitudinal vibration, the temperature of the probe 18 may rise because of the vibration. In this case, the frequency of the longitudinal vibration of the ultrasonic transmitting portion 15 slightly deviates from the reference frequency f0. As a result, the connection position between the intermediary portion 32 and the probe 18 of the ultrasonic transmitting portion 15 slightly deviates from the node position of the longitudinal vibration. Thus, there is a possibility that the longitudinal vibration may be slightly transmitted to the noncontact vibrating portion 31 from the ultrasonic transmitting portion 15 via the intermediary portion 32. Here, in the present embodiment, the axially parallel dimension L0 of the noncontact vibrating portion 31 in directions parallel to the longitudinal axis C is different in value from the natural number multiple of the half wavelength of the longitudinal vibration at the reference frequency f0. Thus, even when the longitudinal vibration is transmitted to the noncontact vibrating portion 31 from the probe 18 via the intermediary portion 32, the noncontact vibrating portion 31 does not perform the longitudinal vibration at the reference frequency 50. Since the noncontact vibrating portion 31 does not perform the longitudinal vibration, the longitudinal vibration is not absorbed by the vibration absorbing portion 38. Therefore, the temperature of the ultrasonic transmitting portion 15 rises, the longitudinal vibration is not damped in the ultrasonic transmitting portion 15, and the ultrasonic transmitting portion 15 can properly perform the longitudinal vibration.

(Modifications of the First Embodiment)

Figure 6:
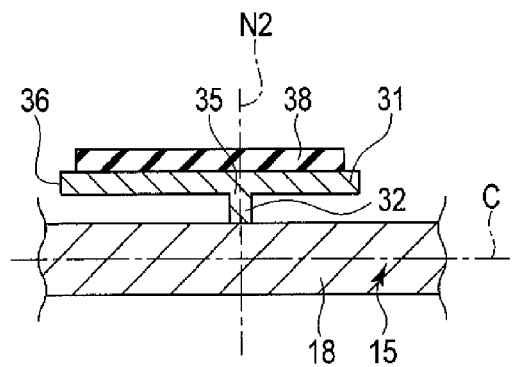
FIG. 6 is a sectional view schematically showing an configuration of an ultrasonic actuated unit according to a first modification of the first embodiment.

Although the noncontact vibrating portion 31 and the vibration absorbing portion 38 are cylindrical in the first embodiment, this is not a limitation. For example, as in a first modification shown in FIG. 6, the noncontact vibrating portion 31 may be plate-shaped. In the present modification as well, the noncontact vibration portion 31 is made of a material having a high vibration transmission capability, and the inaccuracy vibration is transmitted to the farthest portion 36 which is located farthest from the vibration receiving portion 35 in the noncontact vibrating portion 31. The vibration absorbing portion 38 is attached to the noncontact vibrating portion 31 in close contact with a most part of the outer peripheral surface of the noncontact vibrating portion 31. In the present modification as well, the imprecise vibration of the noncontact vibrating portion 31 is absorbed by the vibration absorbing portion 38, and the imprecise vibration is effectively damped in the ultrasonic transmitting portion 15.

In the present modification as well, the intermediary portion 32 is connected to the probe 18 of the ultrasonic transmitting portion 15 at the node position N2 of the longitudinal vibration at the reference frequency f0. Thus, the longitudinal vibration is not transmitted to the intermediary portion 32 from the probe 18, and the longitudinal vibration at the reference frequency f0 in the ultrasonic transmitting portion 15 is not transmitted to the noncontact vibrating portion 31.

Although the intermediary portion 32 is connected to the probe 18 serving as the distal-side transmitting member in the first embodiment, this is not a limitation. For example, as in a second modification shown in FIG. 7, the intermediary portion 32 may be connected to the horn member 16 serving as the proximal-side transmitting member. In the present modification, the noncontact vibrating portion 31 and the vibration absorbing portion 38 are located between the horn member 16 and the vibrator case 2. The vibration absorbing portion 38 is not in contact with the oscillator case 2. Although the intermediary portion 32 and the noncontact vibrating portion 31 are formed separately from the horn member 16 in the present modification, this is not a limitation. For example, the intermediary portion 32 may be integrated with the horn member 16, and the intermediary portion 32 may be continuous with the horn member 16 of the ultrasonic transmitting portion 15.

In the present modification as well, the noncontact vibrating portion 31 is made of a material having a high vibration transmission capability, and the imprecise vibration is transmitted to the farthest portion 36 which is located farthest from the vibration receiving portion 35 in the noncontact vibration portion 31. The vibration absorbing portion 38 is attached to the noncontact vibrating portion 31 in close contact with the outer circumferential surface of the noncontact vibrating portion 31. In the present modification as well, the inaccuracy vibration of the noncontact vibrating portion 31 is absorbed by the vibration absorbing portion 38, and the imprecise vibration is effectively damped in the ultrasonic transmitting portion 15.

In the present modification, the intermediary portion 32 is connected to the horn member 16 of the ultrasonic transmitting portion 15 at the node position N1 of the longitudinal vibration at the reference frequency f0. Thus, the longitudinal vibration is not transmitted to the intermediary portion 32 from the horn member 16, and the longitudinal vibration at the reference frequency 10 in the ultrasonic transmitting portion 15 is not transmitted to the noncontact vibrating portion 31.

(Second Embodiment)

A second embodiment of the present invention is now described with reference to FIG. 8. In the second embodiment, the configuration according to the first embodiment is modified as follows. The same parts as those in the first embodiment are indicated by the same reference signs, and are not described.

FIG. 8 is a diagram showing an internal configuration of a sheath 3 according to the present embodiment. As shown in FIG. 8, according to the present embodiment, an intermediary portion 32 is connected to a probe 18 of an ultrasonic transmitting portion 15 at a node position N2 of longitudinal vibration at a reference frequency f0, as in the first embodiment. A vibration absorbing portion 38 is attached to a noncontact vibrating portion 31. That is, the noncontact vibrating portion 31 and the vibration absorbing portion 38 are located between the probe 18 serving as the distal-side transmitting member and the sheath 3 in diametrical directions.

However, in the present embodiment, a movement regulating portion 41 is provided to the sheath 3. The vibration absorbing portion 38 is in abutment with the movement regulating portion 41 of the sheath 3. The sheath 3 including the movement regulating portion 41 is higher in rigidity than the vibration absorbing portion 38. Thus, the vibration absorbing portion 38 is sandwiched between the movement regulating portion 41 and the noncontact vibrating portion 31. In other words, the vibration absorbing portion 38 intervenes between the noncontact vibrating portion 31 and the sheath 3. The vibration absorbing portion 38 thus is sandwiched between the movement regulating portion 41 (the sheath 3) and the noncontact vibration portion 31, so that the movement of the vibration absorbing portion 38 resulting from the vibration is regulated.

In the present embodiment as well, the imprecise vibration is transmitted to the noncontact vibrating portion 31 from the probe 18 of the ultrasonic transmitting portion 15 via the intermediary portion 32. In the noncontact vibrating portion 31, the inaccuracy vibration is transmitted to the farthest portion 36 which is located farthest from the vibration receiving portion 35. In the present embodiment as well as in the first embodiment, the imprecise vibration of the noncontact vibrating portion 31 is absorbed by the vibration absorbing portion 38. In the present embodiment, the vibration absorbing portion 38 is sandwiched between the movement regulating portion 41 of the sheath 3 and the noncontact vibrating portion 31. Thus, the movement of the vibration absorbing portion 38 resulting from the imprecise vibration is regulated. The movement of the vibration absorbing portion 38 is regulated, so that the imprecise vibration in the noncontact vibrating portion 31 is more effectively damped. Consequently, the imprecise vibration can be more effectively damped in the ultrasonic transmitting portion 15.

(Modification of the Second Embodiment)

Figure 9:
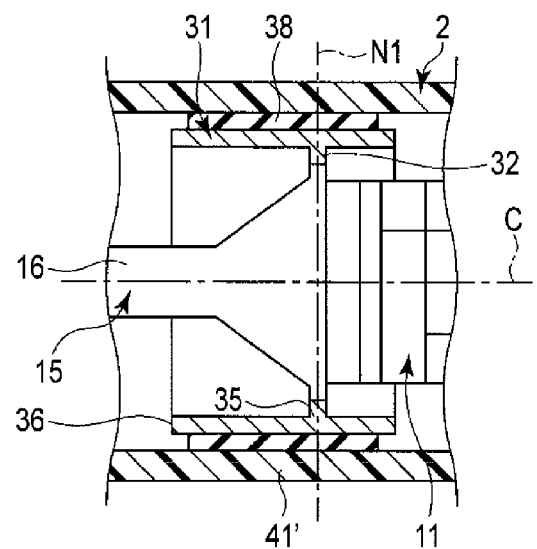
FIG. 9 is a sectional view schematically showing an internal configuration of a vibrator case according to a modification of the second embodiment.

Although the movement regulating portion 41 is provided to the sheath 3 in the second embodiment, this is not a limitation. For example, as in a modification shown in FIG. 9, a movement regulating portion 41' may be provided to a vibrator case 2. In the present embodiment as well as in the second modification of the first embodiment, the intermediary portion 32 is connected to a horn member 16 of the ultrasonic transmitting portion 15 at a node position N1 of the longitudinal vibration at the reference frequency f0. The vibration absorbing portion 38 is attached to the noncontact vibrating portion 31. That is, the noncontact vibrating portion 31 and the vibration absorbing portion 38 are located between the horn member 16 serving as a proximal-side transmitting member and the vibrator case 2 in diametrical directions.

However, in the present modification, the vibration absorbing portion 38 is in abutment with the movement regulating portion 41' of the vibrator case 2. The oscillator case 2 including the movement regulating portion 41' is higher in rigidity than the vibration absorbing portion 38. Thus, the vibration absorbing portion 38 is sandwiched between the movement regulating portion 41' and the noncontact vibrating portion 31. In other words, the vibration absorbing portion 38 intervenes between the noncontact vibration portion 31 and the vibrator case 2. The vibration absorbing portion 38 thus is sandwiched between the movement regulating portion 41' (the vibrator case 2) and the noncontact vibrating portion 31, so that the movement of the vibration absorbing portion 38 resulting from the vibration is regulated.

In the present modification as well, the imprecise vibration is transmitted to the noncontact vibrating portion 31 from the horn member 16 of the ultrasonic transmitting portion 15 via the intermediary portion 32. In the noncontact vibrating portion 31, the imprecise vibration is transmitted to the farthest portion 36 which is located farthest from the vibration receiving portion 35. In the present modification as well as in the first embodiment, the imprecise vibration of the noncontact vibrating portion 31 is absorbed by the vibration absorbing portion 38. In the present modification, the vibration absorbing portion 38 is sandwiched between the movement regulating portion 41' of the vibrator case 2 and the noncontact vibrating portion 31. Thus, the movement of the vibration absorbing portion 38 resulting from the inaccuracy vibration is regulated. The movement of the vibration absorbing portion 38 is regulated, so that the imprecise vibration in the noncontact vibrating portion 31 is more effectively damped. Consequently, the imprecise vibration can be more effectively damped in the ultrasonic transmitting portion 15.

(Other Modifications)

According to the embodiments and modifications described above, the ultrasonic actuated unit 10 (the ultrasonic treatment device 1) has only to include the ultrasonic transmitting portion 15 which is configured to perform a longitudinal vibration having a vibration direction parallel to the longitudinal axis C at the predetermined reference frequency f0 when the ultrasonic vibration is transmitted from the proximal direction to the distal direction, and the intermediary portion 32 which is continuous with the ultrasonic transmitting portion 15 or connected to the ultrasonic transmitting portion 15 at the node position (N1; N2) of the longitudinal vibration. The ultrasonic actuated unit 10 (the ultrasonic treatment device 1) has only to then include the noncontact vibrating portion 31 which is provided without contacting the ultrasonic transmitting portion 15 and to which the imprecise vibration having a vibration direction that is not parallel to the longitudinal axis C is transmitted from the ultrasonic transmitting portion 15 via the intermediary portion 32. The imprecise vibration has only to be transmittable in the noncontact vibrating portion 31. The ultrasonic actuated unit 10 (the ultrasonic treatment device 1) has only to then include the vibration absorbing portion 38 which is attached to the noncontact vibrating portion 31 and which is configured to absorb the imprecise vibration transmitted to the noncontact vibrating portion 31 and thereby damps the imprecise vibration in the ultrasonic transmitting portion 15.

(Reference Examples)

Figure 10:
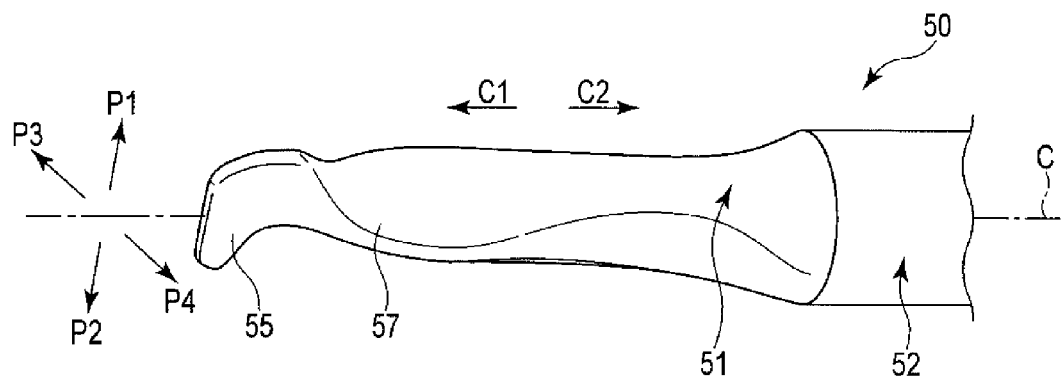
FIG. 10 is a perspective view schematically showing an ultrasonic probe according to a first reference example.
Figure 11:
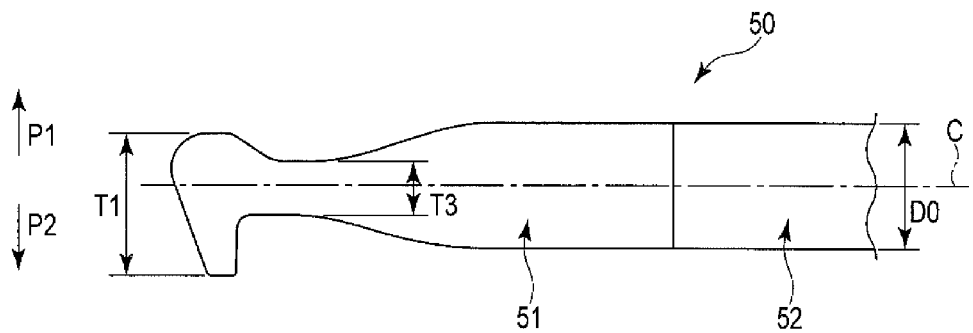
FIG. 11 is a schematic diagram of the ultrasonic probe according to the first reference example seen from a fourth perpendicular direction.
Figure 12:
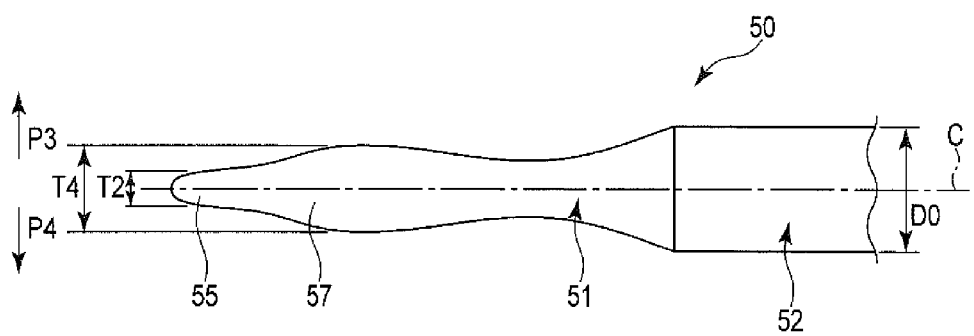
FIG. 12 is a schematic diagram of the ultrasonic probe according to the first reference example seen from a first perpendicular direction.

Now, an ultrasonic probe 50 is described with reference to FIG. 10 to FIG. 12 as a first reference example. FIG. 10 to FIG. 12 are diagrams showing the configuration of the ultrasonic probe 50. The ultrasonic probe 50 extends along a longitudinal axis C. Ultrasonic vibration is thus transmittable from a proximal direction (direction of an arrow C1 in FIG. 10) toward a distal direction (direction of an arrow C2 in FIG. 10).

A distal treatment section 51 is provided in the distal portion of the ultrasonic probe 50. In the distal treatment section 51, a treatment target such as a living tissue is treated by the use of the ultrasonic vibration. A probe body 52 extends in a part located to the proximal direction side of the distal treatment section 51 along the longitudinal axis C. The probe body 52 has a body outside diameter D0. In abdominoscopy, a smallest port into which a treatment device including the ultrasonic probe 50 can be inserted is a minimum port. The diameter at which probe body 52 can be inserted into this minimum port is D1. The body outside diameter D0 of the probe body 52 is a dimension which enables the body to be inserted into the minimum port, and is equal to or less than the diameter D1.

The distal treatment section 51 is provided with a hook-shaped portion 55 which hooks from a first perpendicular direction (direction of an arrow P1 in FIG. 10) perpendicular to the longitudinal axis C toward a second perpendicular direction (direction of an arrow P2 in FIG. 10) opposite to the first perpendicular direction. A treatment target such as a living tissue is hooked to the hook-shaped portion 55, and the treatment target is then treated. The hook-shaped portion 55 has a first hook dimension T1 in the first perpendicular direction and the second perpendicular direction. Directions which are perpendicular to the longitudinal axis C and which are perpendicular to the first perpendicular direction and the second perpendicular direction are a third perpendicular direction (direction of an arrow P3 in FIG. 10) and a fourth perpendicular direction (direction of an arrow P4 in FIG. 10). The hook-shaped portion 55 has a second hook dimension T2 in the third perpendicular direction and the fourth perpendicular direction. The first hook dimension T1 is larger than the second hook dimension T2. The body outside diameter D0 of the probe body 52 is equal to or more than the first hook dimension T1.

In the distal treatment section 51, a dimension varying portion 57 is continuous to the proximal direction side of the hook-shaped portion 55. In the dimension varying portion 57, a first varying dimension in the first perpendicular direction and the second perpendicular direction is reduced from the first hook dimension T1. The first varying dimension of the dimension varying portion 57 decreases toward the proximal direction. The first varying dimension is reduced up to a most reduced dimension T3. In the dimension varying portion 57, a second varying dimension in the third perpendicular direction and the fourth perpendicular direction is increased from the second hook dimension T2. The second varying dimension of the dimension varying portion 57 increases toward the proximal direction. The second varying dimension is increased up to a most increased dimension T4. The most increased dimension T4 is larger than the most reduced dimension T3 and equal to or less than the body outside diameter D0 of the probe body 52.

In the present reference example, the first varying dimension in the first perpendicular direction and the second perpendicular direction is reduced from the first hook dimension T1 in the dimension varying portion 57 which is continuous with the proximal direction side of the hook-shaped portion 55. Thus, in a treatment by the distal treatment section 51, a treatment target such as a living tissue can be easily hooked to the hook-shaped portion 55. The first hook dimension T1 is equal to or less than the body outside diameter D0 of the probe body 52, and the second hook dimension T2 is smaller than the first hook dimension T1. Thus, even when the hook-shaped portion 55 is provided, the distal treatment section 51 is not increased in diameter. Therefore, treatment performance in the distal treatment section 51 is ensured.

In the dimension varying portion 57, the second varying dimension in the third perpendicular direction and the fourth perpendicular direction is increased from the second hook dimension T2. Thus, in the dimension varying portion 57 in which the first varying dimension decreases from the first hook dimension T1, the sectional area perpendicular to the longitudinal axis C does not overly decrease. Therefore, even when the hook-shaped portion 55 and the dimension varying portion 57 are provided, the strength of an ultrasonic probe 30 against the ultrasonic vibration is ensured.

Although the second varying dimension is increased to the most increased dimension T4 in the dimension varying portion 57, the most increased dimension T4 is equal to or less than the body outside diameter D0 of the probe body 52. Thus, even when the dimension varying portion 57 is provided, the distal treatment section 51 is not increased in diameter. Therefore, the treatment performance in the distal treatment section 51 is ensured.

Figure 13:
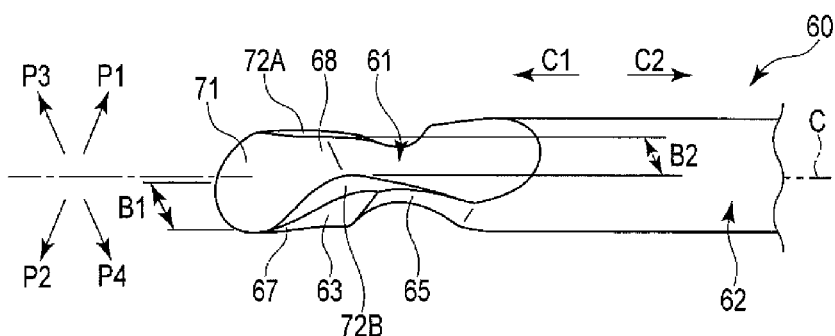
FIG. 13 is a perspective view schematically showing an ultrasonic probe according to a second reference example.
Figure 14:
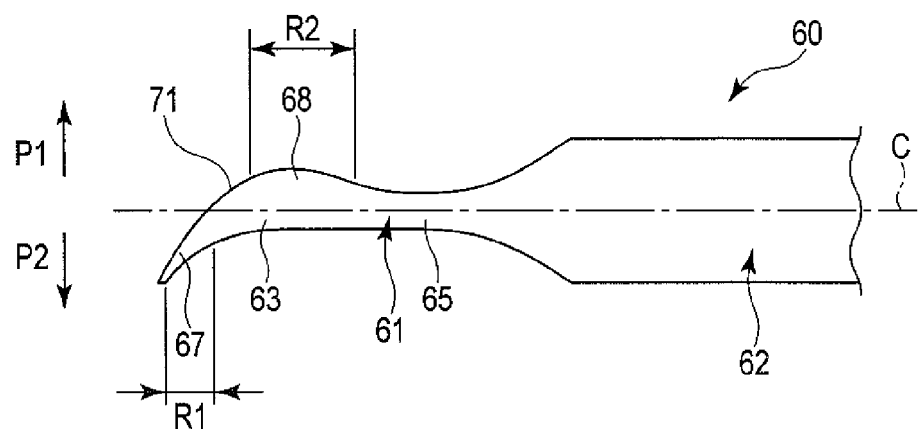
FIG. 14 is a schematic diagram of the ultrasonic probe according to the second reference example seen from a fourth perpendicular direction.

Now, an ultrasonic probe 60 is described with reference to FIG. 13 and FIG. 14 as a second reference example. FIG. 13 and FIG. 14 are diagrams showing the configuration of the ultrasonic probe 60. The ultrasonic probe 60 extends along the longitudinal axis C. An ultrasonic vibration is thus transmittable from a proximal direction (direction of an arrow C1 in FIG. 13) toward a distal direction (direction of an arrow C2 in FIG. 13).

A distal treatment section 61 is provided in the distal portion of the ultrasonic probe 60. In the distal treatment section 61, a treatment target such as a living tissue is treated by the use of the ultrasonic vibration. A probe body 62 extends in a part located to the proximal direction side of the distal treatment section 61 along the longitudinal axis C.

The distal treatment section 61 is provided with a spatulate portion 63, and a plate-shaped portion 65 continuous to the proximal direction side of the spatulate portion 63. The spatulate portion 63 includes a first protrusion 67 which projects from the plate-shaped portion 65 toward a first perpendicular direction (direction of an arrow P1 in FIG. 13) perpendicular to the longitudinal axis C, and a second protrusion 68 which projects from the plate-shaped portion 65 toward a second perpendicular direction (direction of an arrow P2 in FIG. 13) opposite to the first perpendicular direction. The spatulate portion 63 includes a distal curved surface 71 serving as the distal face of the ultrasonic probe 60. The distal curved surface 71 is continuous between a distal end of the first protrusion 67 and a distal end of the second protrusion 68. A position on the distal curved surface 71 is toward the distal direction side as the position on the distal curved surface is toward the first perpendicular direction. The distal curved surface 71 is put in contact with a treatment target such as a living tissue to treat the treatment target.

The first protrusion 67 has a first protrusion axially parallel dimension R1 in directions parallel to the longitudinal axis C. The second protrusion 68 has a second protrusion axially parallel dimension R2 in the directions parallel to the longitudinal axis C. As described above, in the spatulate portion 63 which includes the first protrusion 67, the second protrusion 68, and the distal curved surface 71, the first protrusion axially parallel dimension R1 of the first protrusion 67 is smaller than the second protrusion axially parallel dimension R2 of the second protrusion 68.

Here, directions which are perpendicular to the longitudinal axis C and which are perpendicular to the first perpendicular direction and the second perpendicular direction are a third perpendicular direction (direction of an arrow P3 in FIG. 13) and a fourth perpendicular direction (direction of an arrow P4 in FIG. 13). A chamfering portion 72A is formed in a third-perpendicular-direction-side part of the second protrusion 68. A chamfering portion 72B is formed in the fourth-perpendicular-direction-side part of the second protrusion 68. The first protrusion 67 has a first protrusion width dimension B1 in the third perpendicular direction and the fourth perpendicular direction. The second protrusion 68 has a second protrusion width dimension B2 in the third perpendicular direction and the fourth perpendicular direction. In the present reference example, the chamfered portions 72A and 72B are provided in the second protrusion 68, so that the first protrusion width dimension B1 of the first protrusion 67 is larger than the second protrusion width dimension 52 of the second protrusion 68. Therefore, in the spatulate portion 63 in which the first protrusion axially parallel dimension R1 is smaller than the second protrusion axially parallel dimension R2, the mass of the first protrusion 67 is substantially the same as the mass of the second protrusion 68.

Since the mass of the first protrusion 67 is substantially the same as the mass of the second protrusion 68, the center of gravity of the spatulate portion 63 (the distal treatment section 61) is effectively prevented from greatly deviating from the longitudinal axis C in the first perpendicular direction and the second perpendicular direction. The center of gravity of the spatulate portion 63 does not greatly deviate from the longitudinal axis C, so that even when the spatulate portion 63 including the distal curved surface 71 is provided, the stability of the ultrasonic vibration of the ultrasonic probe 60 is ensured. Therefore, even when the spatulate portion 63 is provided, the strength of the ultrasonic probe 60 against the ultrasonic vibration is ensured.

The distal curved surface 71 is continuous between the distal end of the first protrusion 67 and the distal end of the second protrusion 68. Thus, the dimension of the distal curved surface 71 in the first perpendicular direction and the second perpendicular direction is larger. Therefore, the treatment target is efficiently treated by the use of the distal curved surface 71.

Figure 15:
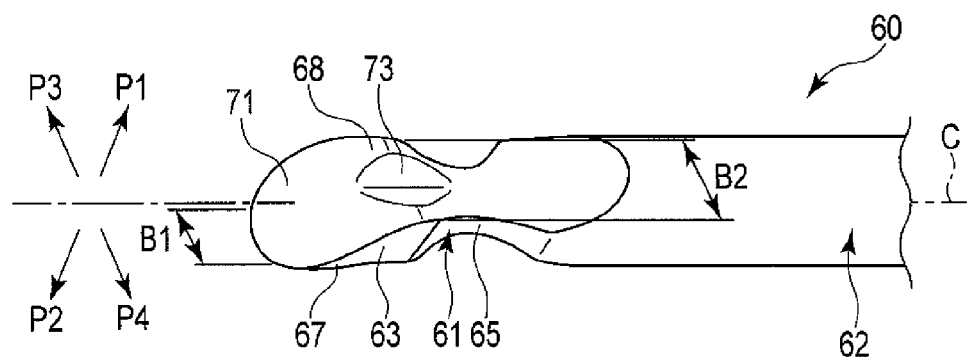
FIG. 15 is a perspective view schematically showing an ultrasonic probe according to a third reference example.

Although the chamfered portions 72A and 72B are formed in the second protrusion 68 in the second reference example, this is not a limitation. For example, as in a third reference example shown in FIG. 15, a concaved portion 73 concaved in a first perpendicular direction (direction of an arrow P1 in FIG. 15) may be provided in the second protrusion 68 instead of the chamfered portions 72A and 72B.

In the present reference example as well as in the second reference example, the first protrusion axially parallel dimension R1 of the first protrusion 67 is smaller than the second protrusion axially parallel dimension R2 of the second protrusion 68. In the present reference example, the first protrusion width dimension B1 of the first protrusion 67 is substantially the same as the second protrusion width dimension B2 of the second protrusion 68. However, since the concaved portion 73 is provided in the present reference example, the mass of the first protrusion 67 is substantially the same as the mass of the second protrusion 68. That is, even in the spatulate portion 63 in which the first protrusion axially parallel dimension R1 is smaller than the second protrusion axially parallel dimension R2, the mass of the first protrusion 67 is substantially the same as the mass of the second protrusion 68.

Therefore, in the present reference example as well as in the second reference example, the center of gravity of the spatulate portion 63 (the distal treatment section 61) is effectively prevented from greatly deviating from the longitudinal axis C in the first perpendicular direction and the second perpendicular direction. The center of gravity of the spatulate portion 63 does not greatly deviate from the longitudinal axis C, so that even when the spatulate portion 63 including the distal curved surface 71 is provided, the stability of the ultrasonic vibration of the ultrasonic probe 60 is ensured. Therefore, even when the spatulate portion 63 is provided, the strength of the ultrasonic probe 60 against the ultrasonic vibration is ensured.

In the present reference example as well as in the second reference example, the distal curved surface 71 is continuous between the distal end of the first protrusion 67 and the distal end of the second protrusion 68. Thus, the dimension of the distal curved surface 71 in the first perpendicular direction and the second perpendicular direction is larger. Therefore, the treatment target is efficiently treated by the use of the distal curved surface 71.

Characteristic technical matters according to the reference examples are additionally set forth below.

Notes (Additional Note 1)

An ultrasonic probe which extends along a longitudinal axis and which is configured to transmit an ultrasonic vibration from a proximal direction to a distal direction, the ultrasonic probe comprising:

a distal treatment section provided in a distal portion;

a hook-shaped portion which is provided in the distal treatment section and which hooks from a first perpendicular direction perpendicular to the longitudinal axis toward a second perpendicular direction opposite to the first perpendicular direction, the hook-shaped portion having a first hook dimension in the first perpendicular direction and the second perpendicular direction, the hook-shaped portion having a second hook dimension in a third perpendicular direction and a fourth perpendicular direction which are directions perpendicular to the longitudinal axis and perpendicular to the first perpendicular direction and the second perpendicular direction; and a dimension varying portion continuous with a proximal direction side of the hook-shaped portion in the distal treatment section, a first varying dimension in the first perpendicular direction and the second perpendicular direction being reduced from the first hook dimension in the dimension varying portion, a second varying dimension in the third perpendicular direction and the fourth perpendicular direction being increased from the second hook dimension in the dimension varying portion.

(Additional Note 2)

The ultrasonic probe according to Additional note 1, wherein the first hook dimension is larger than the second hook dimension, and in the dimension varying portion, the first varying dimension is reduced up to a most reduced dimension, and the second varying dimension is increased up to a most increased dimension larger than the most reduced dimension.

(Additional Note 3)

The ultrasonic probe according to Additional note 1, further comprising a probe body extending in a part located to the proximal direction side of the distal treatment section along the longitudinal axis, the probe body having a body outside diameter equal to or more than the first hook dimension.

(Additional Note 4)

The ultrasonic probe according to Additional note 3, wherein in the dimension varying portion, the second varying dimension is increased to a most increased dimension equal to or less than the body outside diameter.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic actuated unit comprising:
   a sheath;
   an ultrasonic transmitting portion that is disposed within the sheath and that extends along a longitudinal axis, the ultrasonic transmitting portion being configured to perform a longitudinal vibration,
      the longitudinal vibration having a vibration direction parallel to the longitudinal axis at a predetermined reference frequency when an ultrasonic vibration is transmitted from a proximal direction toward a distal direction of the ultrasonic actuated unit;
   an intermediary portion that is connected to the ultrasonic transmitting portion at a node position of the longitudinal vibration such that the intermediary portion does not contact the sheath;
   a noncontact vibrating portion that extends parallel to the longitudinal axis without contacting the ultrasonic transmitting portion,
      the intermediary portion being configured to transmit an imprecise vibration to the noncontact vibrating portion from the ultrasonic transmitting portion, the imprecise vibration having a vibration direction that is not parallel to the longitudinal axis,
      a length of the noncontact vibrating portion being greater than a length of the intermediary portion such that the length of the noncontact vibrating portion and the length of the intermediary portion are parallel to the longitudinal axis, and
      the length of the noncontact vibrating portion being different in value from a natural number multiple of a half wavelength of the longitudinal vibration at the reference frequency in a direction parallel to the longitudinal axis so that the noncontact vibrating portion does not perform the longitudinal vibration at the reference frequency when the ultrasonic vibration is transmitted via the intermediary portion;
   a vibration absorbing portion that is attached to the noncontact vibrating portion and that is configured to absorb the imprecise vibration transmitted to the noncontact vibrating portion.

2. The ultrasonic actuated unit according to claim 1, wherein;
   the noncontact vibrating portion includes a vibration receiving portion that is connected to the intermediary portion, and
   the noncontact vibrating portion includes a farthest portion that is provided at a position on the noncontact vibrating portion farthest from the vibration receiving portion, the imprecise vibration being transmitted from the vibration receiving portion to the farthest portion.

3. The ultrasonic actuated unit according to claim 2, wherein the noncontact vibrating portion (i) is equal in vibration transmission capability to the ultrasonic transmitting portion or (ii) is higher in vibration transmission capability than the ultrasonic transmitting portion.

4. The ultrasonic actuated unit according to claim 3, wherein the noncontact vibrating portion is made of a material that is (i) equal in vibration transmission capability to PEEK or that is (ii) higher in vibration transmission capability than PEEK.

5. The ultrasonic actuated unit according to claim 1, wherein the vibration absorbing portion is lower in vibration transmission capability than the noncontact vibrating portion.

6. The ultrasonic actuated unit according to claim 1, further comprising a movement regulating portion, the movement regulating portion being higher in rigidity than the vibration absorbing portion and sandwiching the vibration absorbing portion between the movement regulating portion and the noncontact vibrating portion so that the movement regulating portion is configured to regulate a movement of the vibration absorbing portion resulting from the imprecise vibration.

7. The ultrasonic actuated unit according to claim 1, wherein the noncontact vibrating portion extends at least one of proximally and distally of the intermediary portion in directions that are parallel to the longitudinal axis.

8. The ultrasonic actuated unit according to claim 1, wherein the noncontact vibrating portion extends proximally and distally of the intermediary portion in directions that are parallel to the longitudinal axis.

9. The ultrasonic actuated unit according to claim 1, wherein the vibration absorbing portion is attached to an outer peripheral portion of the noncontact vibrating portion without contacting the ultrasonic transmitting portion.

10. An ultrasonic treatment device comprising:
    the ultrasonic actuated unit according to claim 6; and
    an ultrasonic generating portion that is attached to the ultrasonic transmitting portion and that is configured to generate the ultrasonic vibration and to transmit the generated ultrasonic vibration to the ultrasonic transmitting portion,
    wherein the ultrasonic transmitting portion includes;
       a proximal-side transmitting member that is attached to the ultrasonic generating portion, the ultrasonic vibration being transmitted from the ultrasonic generating portion to the proximal-side transmitting member, and
       a distal-side transmitting member that is connected to a distal direction side of the proximal-side transmitting member, the ultrasonic vibration being transmitted from the proximal-side transmitting member to the distal-side transmitting member.

11. The ultrasonic treatment device according to claim 10, wherein:
    the sheath partly serves as the movement regulating portion and through which the distal-side transmitting member is inserted, and
    the noncontact vibrating portion and the vibration absorbing portion are located between the distal-side transmitting member and the sheath in diametrical directions.

12. The ultrasonic treatment device according to claim 10, further comprising a vibrator case that partly serves as the movement regulating portion and inside which the ultrasonic generating portion and the proximal-side transmitting member are provided, wherein the noncontact vibrating portion and the vibration absorbing portion are located between the proximal-side transmitting member and the vibrator case in diametrical directions.

13. An ultrasonic treatment device comprising:
the ultrasonic actuated unit according to claim 1; and
an ultrasonic generating portion that is attached to the ultrasonic transmitting portion and that is configured to generate the ultrasonic vibration and to transmit the generated ultrasonic vibration to the ultrasonic transmitting portion.

* * * * *